US007011687B2

(12) United States Patent
Deffenbaugh et al.

(10) Patent No.: US 7,011,687 B2
(45) Date of Patent: Mar. 14, 2006

(54) ANKLE PROSTHESIS WITH A FRONT LOADING BEARING AND ASSOCIATED METHOD

(75) Inventors: Daren Deffenbaugh, Winona Lake, IN (US); Brian Maroney, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 97 days.

(21) Appl. No.: 10/337,135

(22) Filed: Jan. 6, 2003

(65) Prior Publication Data

US 2004/0133282 A1    Jul. 8, 2004

(51) Int. Cl.
*A61F 2/42*    (2006.01)
(52) U.S. Cl. .................................................. 623/21.18
(58) Field of Classification Search ... 623/21.11–21.19
See application file for complete search history.

(56) References Cited

U.S. PATENT DOCUMENTS

| | | | |
|---|---|---|---|
| 3,889,300 A | | 6/1975 | Smith |
| 3,987,500 A | | 10/1976 | Schlein |
| 4,069,518 A | | 1/1978 | Groth, Jr. et al. |
| 4,470,158 A | * | 9/1984 | Pappas et al. ........... 623/20.21 |
| 4,731,087 A | * | 3/1988 | Sculco et al. ............ 623/21.15 |
| 5,041,139 A | | 8/1991 | Branemark |
| 5,326,365 A | * | 7/1994 | Alvine ..................... 623/21.18 |
| 5,766,259 A | * | 6/1998 | Sammarco ............... 623/21.18 |
| 5,824,106 A | | 10/1998 | Fournol |
| 6,183,519 B1 | | 2/2001 | Bonnin et al. |
| 6,409,767 B1 | * | 6/2002 | Perice et al. ............. 623/21.18 |
| 6,485,520 B1 | * | 11/2002 | Hubach et al. .......... 623/21.13 |
| 2003/0204265 A1 | * | 10/2003 | Short et al. .............. 623/21.18 |

FOREIGN PATENT DOCUMENTS

| | | |
|---|---|---|
| EP | 0 864 304 A1 | 9/1998 |
| FR | 2 759 900 | 8/1998 |
| WO | WO 01/30264 A2 | 5/2001 |

* cited by examiner

*Primary Examiner*—Pedro Philogene
(74) *Attorney, Agent, or Firm*—Maginot, Moore & Beck

(57) ABSTRACT

An ankle prosthesis includes a tibial component attachable to a tibia. A bearing component is movable in an anterior-to-posterior direction to thereby engage and become releasably attached to the tibial component. The bearing component can be released from the tibial component by movement in a posterior-to-anterior direction to thereby be removed from the tibial component.

20 Claims, 20 Drawing Sheets

ANKLE PROSTHESIS WITH A FRONT LOADING BEARING AND ASSOCIATED METHOD

BACKGROUND OF THE INVENTION

The present invention relates to prosthetic systems for the replacement of joints or portions thereof. More particularly, the invention concerns an ankle prosthesis system that can be used in the extremities that have experienced bone loss or significant, irreparable bone trauma.

For treatment of various problems with the ankle such as degenerative arthritis and trauma of the ankle, total ankle replacement, or "arthroplasty" is rapidly becoming a common course of action. One method of providing relief to a patient is to replace the articulating surfaces of the ankle, i.e. the inferior articular surface of the tibia and the articular surface of the talus. The inferior articular surface of the tibia can be replaced with a concave shaped surface, often utilizing a polymer material, and the articular surface of the talus is replaced with a convex shaped surface. The polymer used can be polyethylene, for example. In such replacement, pain relief, increased motion and anatomic reconstruction of the ankle joint are goals of the orthopaedic surgeon.

There are two basic types of ankle replacements: unconstrained meniscal bearing ankle prostheses and semi-constrained fixed bearing ankle prostheses. Semi-constrained fixed bearing ankle prostheses include one articulating interface, i.e., the interface between the concave polymer bearing surface and the convex articulating surface. In semi-constrained prostheses, the concave polymer bearing is locked in place relative to the tibia. In contrast, unconstrained meniscal bearing ankle prostheses include two articulating interfaces, allowing additional degrees of freedom. One articulating interface is between a tibial component and a meniscal bearing. The other articulating interface is between the meniscal bearing and a talar component. Examples of unconstrained meniscal bearing ankle prostheses are the S.T.A.R. prosthesis from Link, and the Beuchel-Pappas ankle from Endotech, both of which are loaded from the front of the ankle. A problem with such unconstrained ankle prostheses is that ankle stability is highly dependent on the surrounding soft tissues. Specifically, the meniscal polymer bearing can become dislocated in poorly balanced total ankle replacements.

An example of a semi-constrained fixed bearing ankle prosthesis is the Agility Ankle by DePuy. In assembling the prosthesis, the concave polymer bearing is placed into a tibial component from an inferior direction moving superiorly. That is, the concave polymer bearing is put in (loaded) from the bottom. The concave polymer bearing is held in place by columns having a superior-inferior orientation. These columns prevent the implant from translating under a load in an anterior direction or a posterior direction.

With use, components of prosthetic systems wear out or break and thus need to be periodically replaced. It is desirable for the prosthetic systems to be designed such that components that may potentially wear out are easily removed from the patient's body and easily replaced by the surgeon. With known semi-constrained ankles, such as the Agility Ankle, removing the concave polymer bearing requires the surgeon to cut off the superior-inferior oriented columns with a reciprocating saw or some other instrument. The sawing generates undesirable polymer debris, which may not be fully removed during the surgery.

Consequently, there is a need for a semi-constrained ankle prosthesis system having a replaceable bearing component that is easily removed and inserted by the surgeon.

SUMMARY OF THE INVENTION

In order to address these needs, the present invention provides a semi-constrained ankle prosthesis having a replaceable bearing component. The replaceable bearing component is removable from a tibial component of the semi-constrained ankle prosthesis in a posterior-to-anterior direction and insertable into the tibial component in an anterior-to-posterior direction. The bearing component is releasably locked into the tibial component by an interference-type locking mechanism.

In one form, the subject invention provides an ankle prosthesis including a tibial component attachable to a tibia. A bearing component is moved in an anterior-to-posterior direction to thereby engage and become snap-locked to the tibial component. The bearing component can be unlocked from the tibial component and moved in a posterior-to-anterior direction to thereby become disengaged from the tibial component.

In another form, the subject invention provides an ankle prosthesis including a tibial component attachable to a tibia. A bearing component of the ankle prosthesis has a concave articulating surface and is moved in an anterior-to-posterior direction to thereby engage and become releasably fixed to the tibial component. A talar component of the ankle prosthesis has a convex articulating surface engaging the concave articulating surface of the bearing component.

In yet another form, the subject invention provides an ankle prosthesis including a tibial component attachable to a tibia. A bearing component of the ankle prosthesis is moved in an anterior-to-posterior direction to thereby engage and become fixed to the tibial component.

An advantage of the present invention is that the surgeon can easily remove the bearing component from the tibial component after implantation of the ankle prosthesis into the patient's ankle, and can easily place a new bearing component into the tibial component in the patient's ankle.

Another advantage is that there is no need to saw any part of the prosthesis in order to replace the bearing component.

Yet another advantage is that the semi-constrained ankle prosthesis of the present invention provides more ankle stability than does an unconstrained ankle prosthesis.

DESCRIPTION OF THE FIGURES

Corresponding reference characters indicate corresponding parts throughout the figures.

DESCRIPTION OF THE PREFERRED EMBODIMENTS

Figure 1:
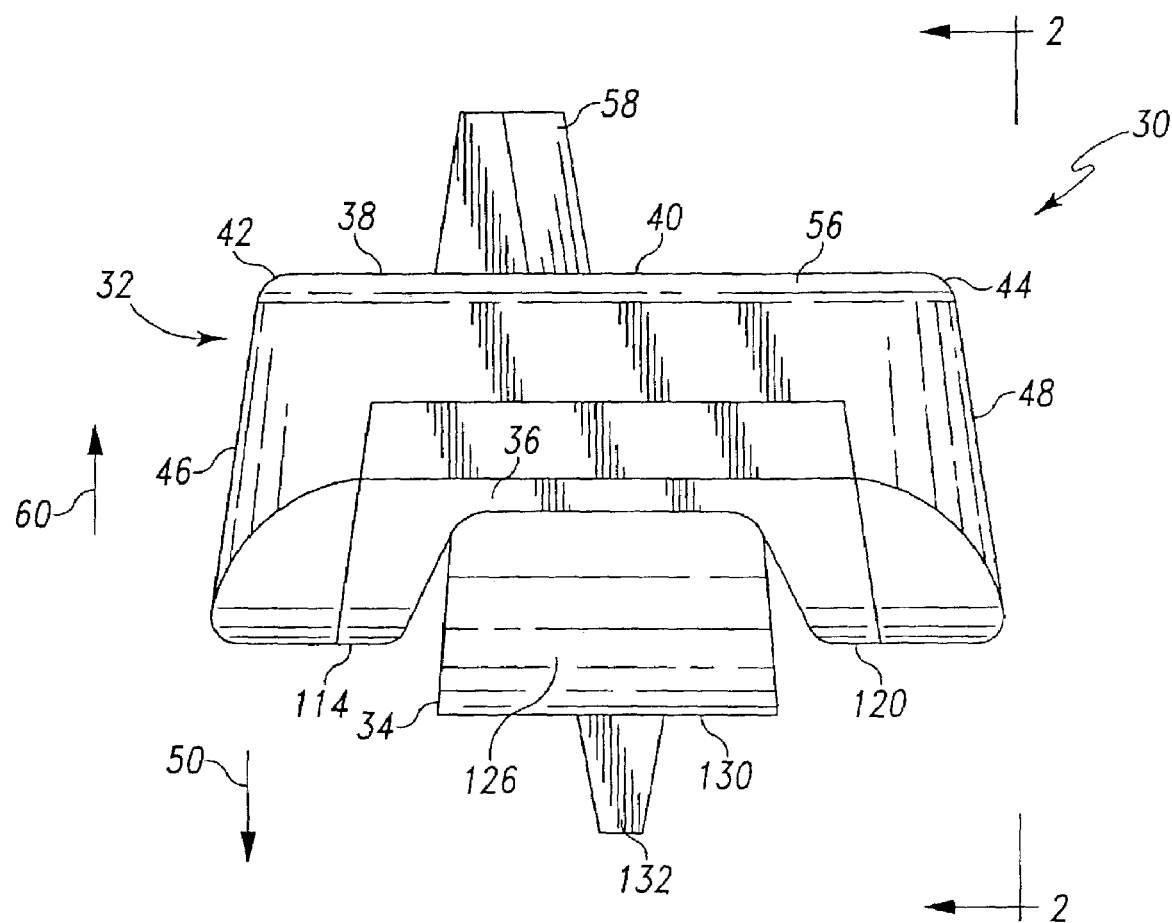
FIG. 1 is a rear view of an ankle replacement or prosthesis in accordance with one embodiment of the present invention.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring to FIG. 1, there is depicted one embodiment of the subject invention. Particularly, there is depicted an ankle prosthesis generally designated 30. While the present invention is shown and described with respect to an ankle, it should be understood that the principles of the subject invention as described herein are applicable to prostheses for joints other than the ankle, particularly for articulating surface joints similar to the ankle. The ankle prosthesis 30 is for a right ankle. An ankle prosthesis for a left ankle would be a mirror image of the ankle prosthesis 30. The ankle prosthesis 30 is configured for replacement surgery wherein the patient's ankle joint is replaced. The ankle prosthesis 30 includes a tibial assembly 32 and a talar component 34 which interact to provide flexion and extension similar to that of a normal ankle. The ankle prosthesis 30 is compact so as to require minimal removal of the patient's bone and tissue.

Figure 2:
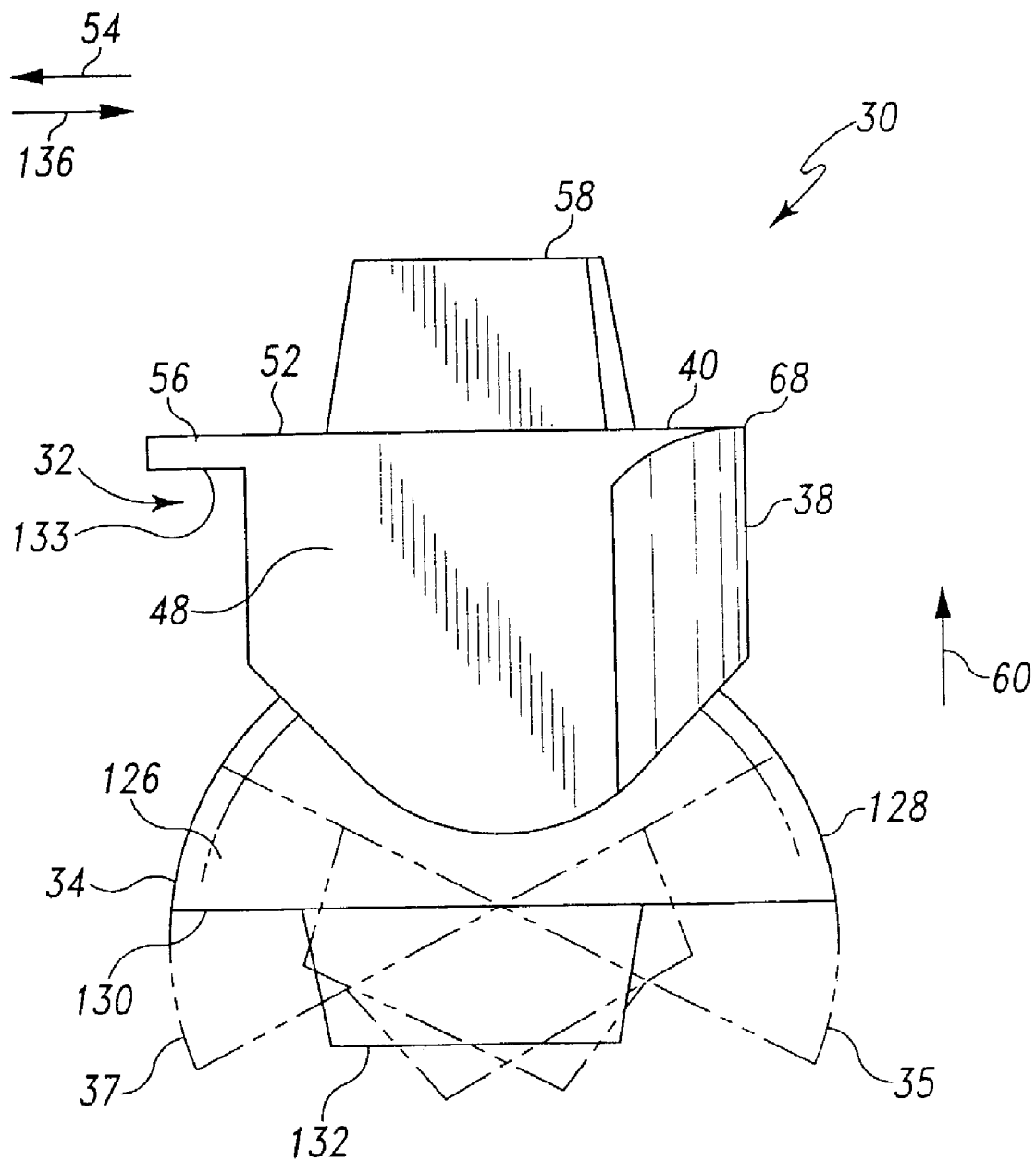
FIG. 2 is a side view of the ankle prosthesis along line 2—2 in FIG. 1 depicting movement of a talar component relative to a tibial assembly.

The tibial assembly 32 attaches to a patient's tibia, and the talar component 34 attaches to a patient's talus. The talar component 34 slidingly engages the tibial assembly 32 and pivots with respect thereto, as indicated in FIG. 2. The talar component 34 can pivot between a flexed position 35 and an extended position 37 to thereby provide the patient with approximately the same range of movement as that of a natural ankle.

The tibial assembly 32 includes a bearing component 36 which fits into and is releasably held by a tibial component 38. The tibial component 38 includes a base plate or superior wall 40 having a medial edge 42 and a lateral edge 44. Positioning walls including a medial wall 46 and a lateral wall 48 extend from the medial edge 42 and the lateral edge 44, respectively, in a superior-to-inferior direction 50. Extending from a posterior edge 52 of the superior wall 40 in an anterior-to-posterior direction 54 is a triangular extension 56. A projection in the form of a tibial fin 58 extends from the superior wall 40 in an inferior-to-superior direction 60.

Figure 3:
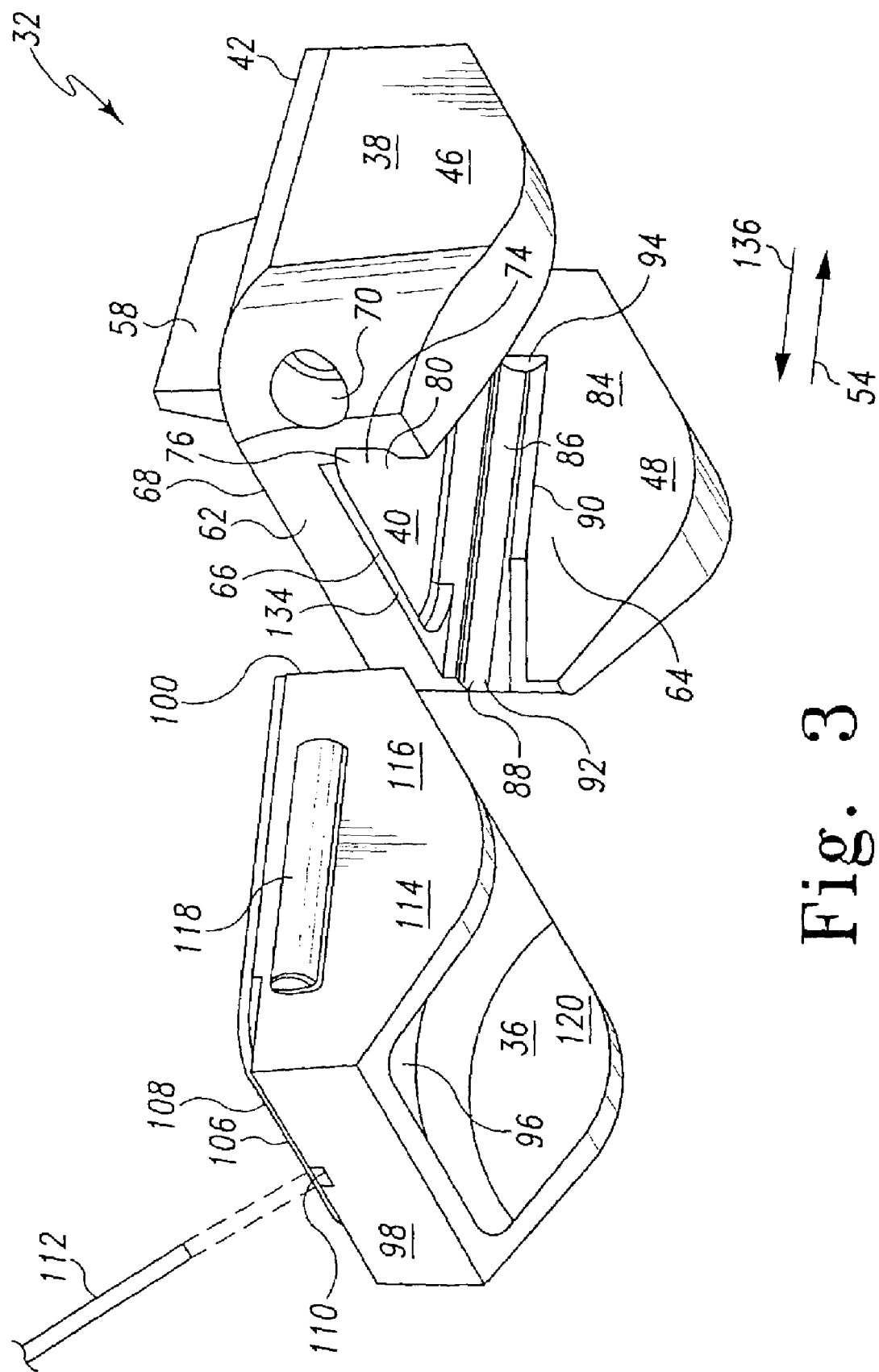
FIG. 3 is a perspective, exploded view of the tibial assembly of FIG. 1.
Figure 4:
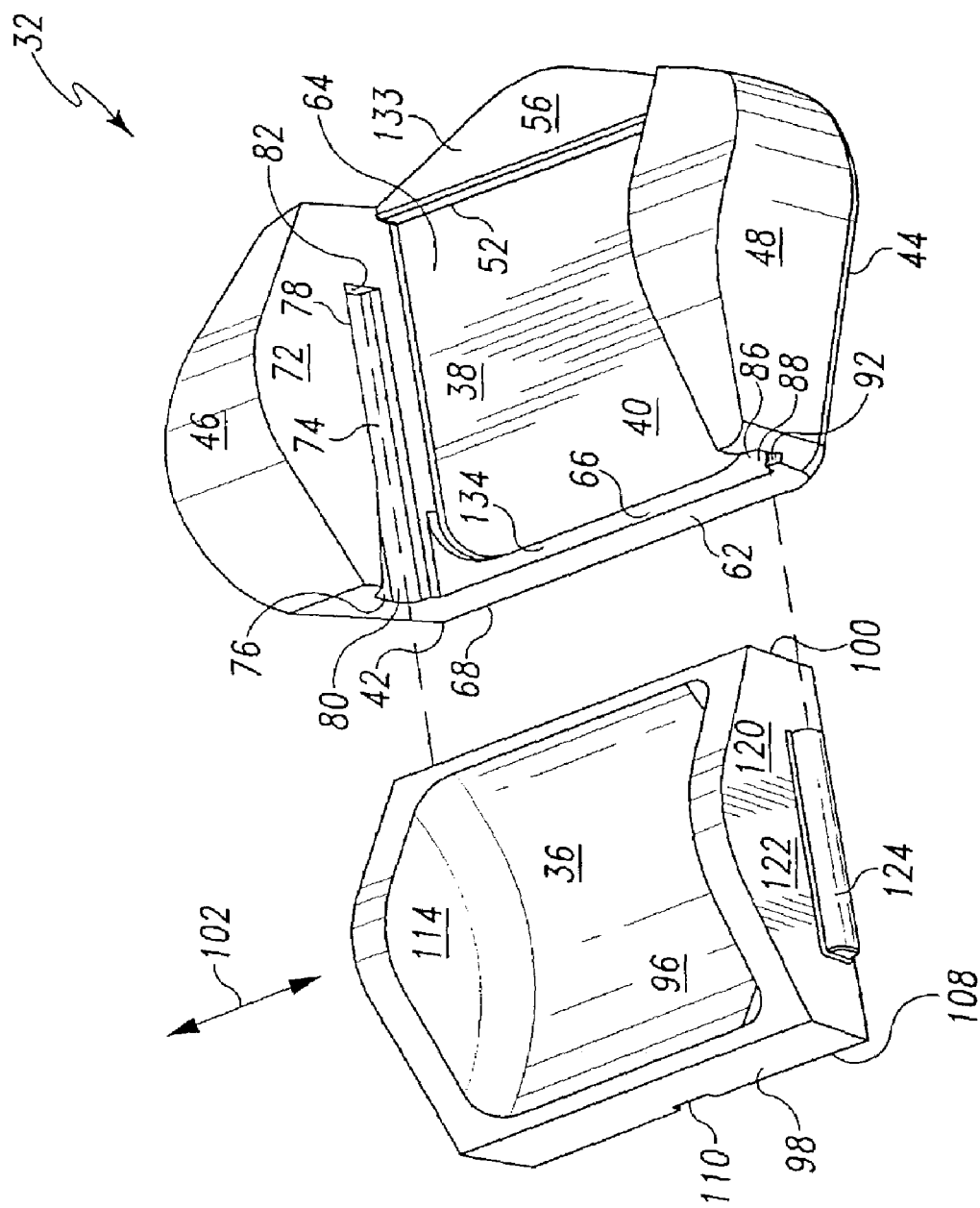
FIG. 4 is another perspective, exploded view of the tibial assembly of FIG. 1.
Figure 5:
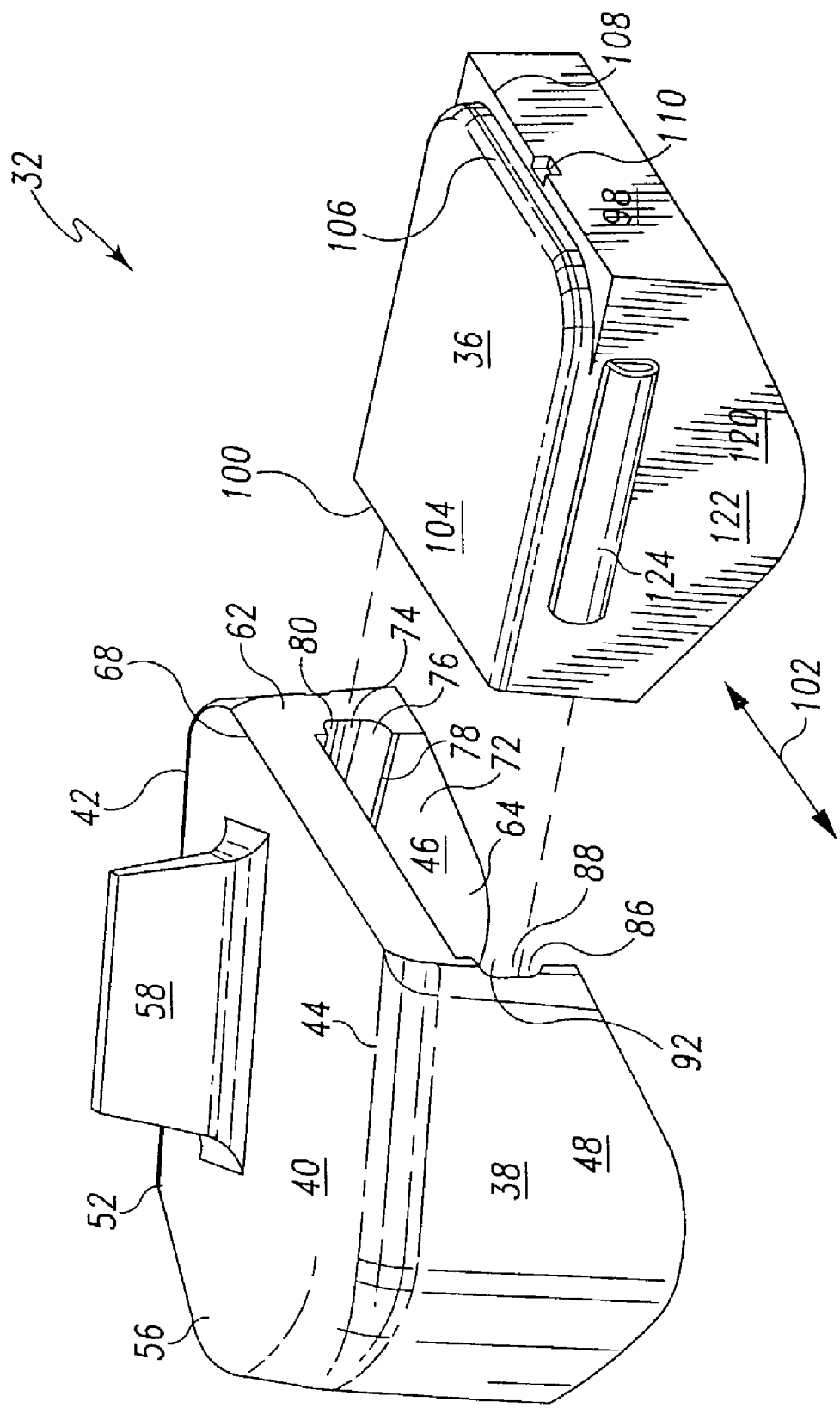
FIG. 5 is yet another perspective, exploded view of the tibial assembly of FIG. 1.

As best seen in FIGS. 3–5, an anterior side 62 of the tibial component 38 has an opening 64 for receiving the bearing component 36. A releasable attachment element such as a snap-locking element in the form of a retaining wall 66 extends from an anterior edge 68 of the superior wall 40 in the superior-to-inferior direction 50. The anterior side 62 of the tibial component 38 includes a threaded screw hole 70 extending into the medial wall 46. An externally threaded implanting tool (not shown) can engage the screw hole 70 in order to guide the tibial assembly 32 into the patient's ankle. An inner surface 72 of the medial wall 46 includes a medial slot 74 having an anterior-posterior orientation and an opening 76 in the anterior side 62. An inferior edge 78 of the slot 74 is nonlinear such that the slot 74 is wider at an anterior end 80 than at a posterior end 82. An inner surface 84 of the lateral wall 48 includes a lateral slot 86 having an anterior-posterior orientation and an opening 88 in the anterior side 62. An inferior edge 90 of the slot 86 is nonlinear such that the slot 86 is wider at an anterior end 92 than at a posterior end 94. In the embodiment shown, the slots 74 and 86 are mirror images of each other.

The bearing component 36 is formed of a resilient material, such as plastic. In particular, the bearing component 36 can be formed of polyethylene. The bearing component 36 includes a concave articulating surface 96 for interfacing with the talar component 34. The concave articulating surface 96 faces in the superior-to-inferior direction 50. The concave articulating surface 96 forms an arc from an anterior side 98 to a posterior side 100 of the bearing component 36 such that a cross section of the surface 96 is constant along a medial-lateral axis 102. A superior surface 104 of the bearing component 36 drops down or steps down adjacent the anterior side 98 to thereby form a releasable attachment element or snap-locking element in the form of a latch 106 extending parallel to the medial-lateral axis 102. A superior edge 108 of the anterior side 98 includes a notch 110 for receiving a removal tool 112, as described in more detail below.

A medial side portion 114 of the bearing component 36 includes an outer surface 116 having a medial rib 118 with an anterior-posterior orientation. Similarly, a lateral side portion 120 of the bearing component 36 includes an outer surface 122 having a lateral rib 124 with an anterior-posterior orientation. The bearing component 36 is sized to fit within the opening 64 of the tibial component 38. The medial rib 118 and the lateral rib 124 are sized to fit within the medial slot 74 and the lateral slot 86, respectively.

The talar component 34 includes a dome portion 126 having a convex articulating surface in the form of a semicircular curving surface 128. A flat inferior side 130 of the talar component 34 has a projection in the form of a talar fin 132 extending in the superior-to-inferior direction 50. The bearing component 36 and the dome portion 126 provide a range of motion of approximately sixty degrees between an extended position and a flexed position, as shown in FIG. 2.

Referring again to FIG. 1, it can be seen that the side portions 114, 120 and the walls 46, 48 retain the talar component 34 from lateral sliding at all positions. The walls 46, 48 provide support to the joint so that the ankle prosthesis 30 remains properly positioned at all times. The ankle prosthesis 30 pivots at the meeting of the dome portion 126 and the bearing component 36. The surfaces 96, 128 slide relative to one another and allow pivoting to occur, thereby having a motion and range of motion similar to that of a natural ankle joint.

Figure 6:
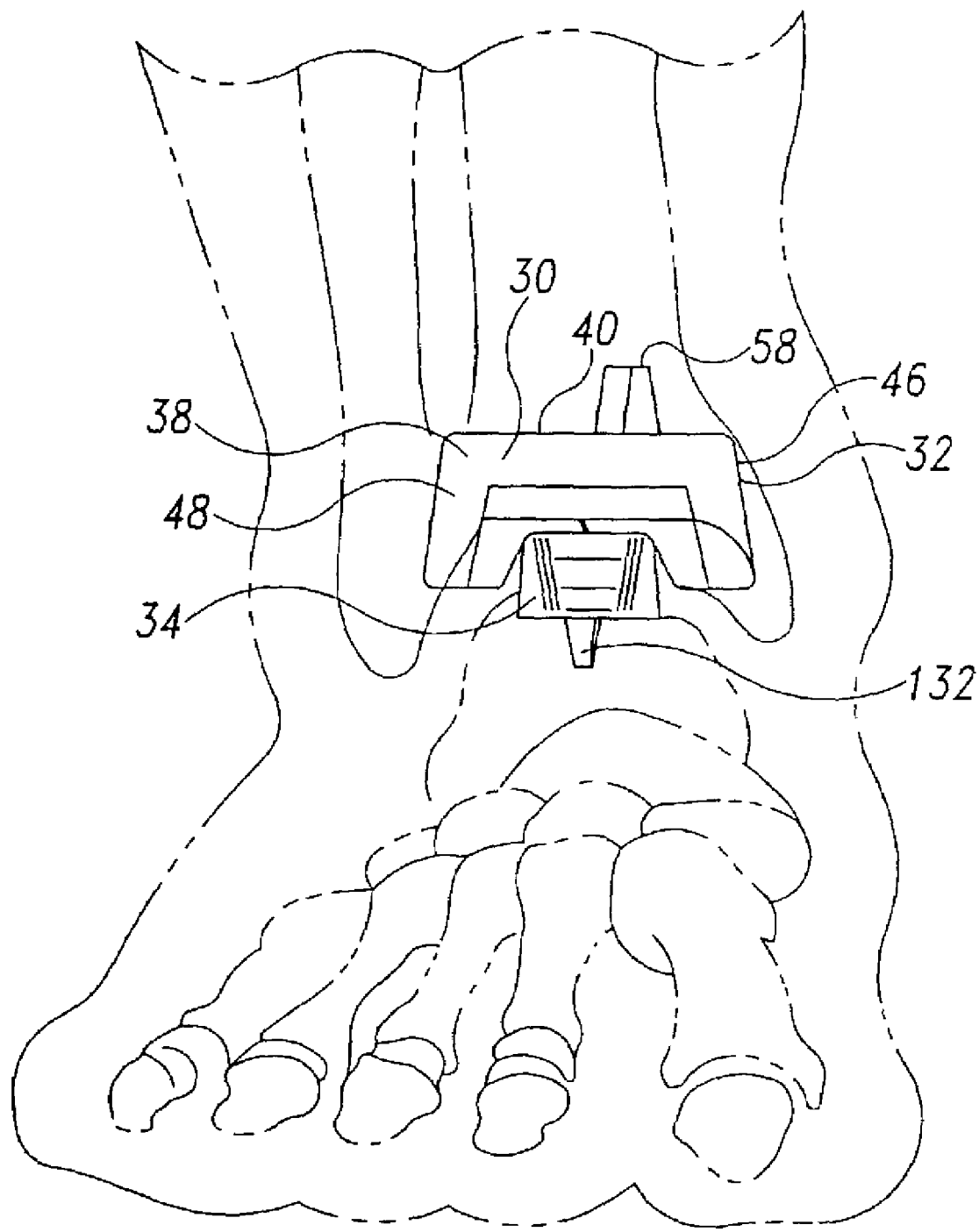
FIG. 6 is a front view of the ankle prosthesis of FIG. 1 implanted in a patient's ankle.

The tibial component 38 must be wide enough to bridge the area between the tibia and the fibula, as shown in FIG. 6. When implanted, the lateral wall 48 butts up against the fibula while the medial wall 46 butts up against the medial malleolus. In this manner, the fibula fuses to the tibia and a portion of the weight bearing is transferred to the fibula. An inferior surface 133 of the extension 56 is supported by bone, thereby inhibiting migration of the tibial assembly 32 in the superior-to-inferior direction 50. The superior wall 40 should be as thin as possible to minimize bone removal for implantation while maintaining sufficient strength to withstand the forces to which it is subjected.

During assembly, the bearing component 36 is moved in the anterior-to-posterior direction 54 to thereby engage the tibial component 38. More particularly, the medial rib 118 and the lateral rib 124 are slid into the medial slot 74 and the lateral slot 86, respectively. The slots 74, 86 become narrower as the ribs 118, 124 progress therein in the anterior-to-posterior direction 54. That is, the inferior edges 78, 90 of the slots 74, 86 rise in the inferior-to-superior direction 60 along the anterior-to-posterior direction 54. Thus, the inferior edges 78, 90 get closer to the inferior surface 134 of the retaining wall 66 along the anterior-to-posterior direction 54. The bias of the inferior edges 78, 90 of the slots 74, 86 against the ribs 118, 124 pushes the bearing component 36 in the inferior-to-superior direction 60. This causes the superior surface 104 of the bearing component 36 to become biased against the inferior surface 134 of the retaining wall 66 as the ribs 118, 124 progress in the anterior-to-posterior direction 54.

Figure 7:
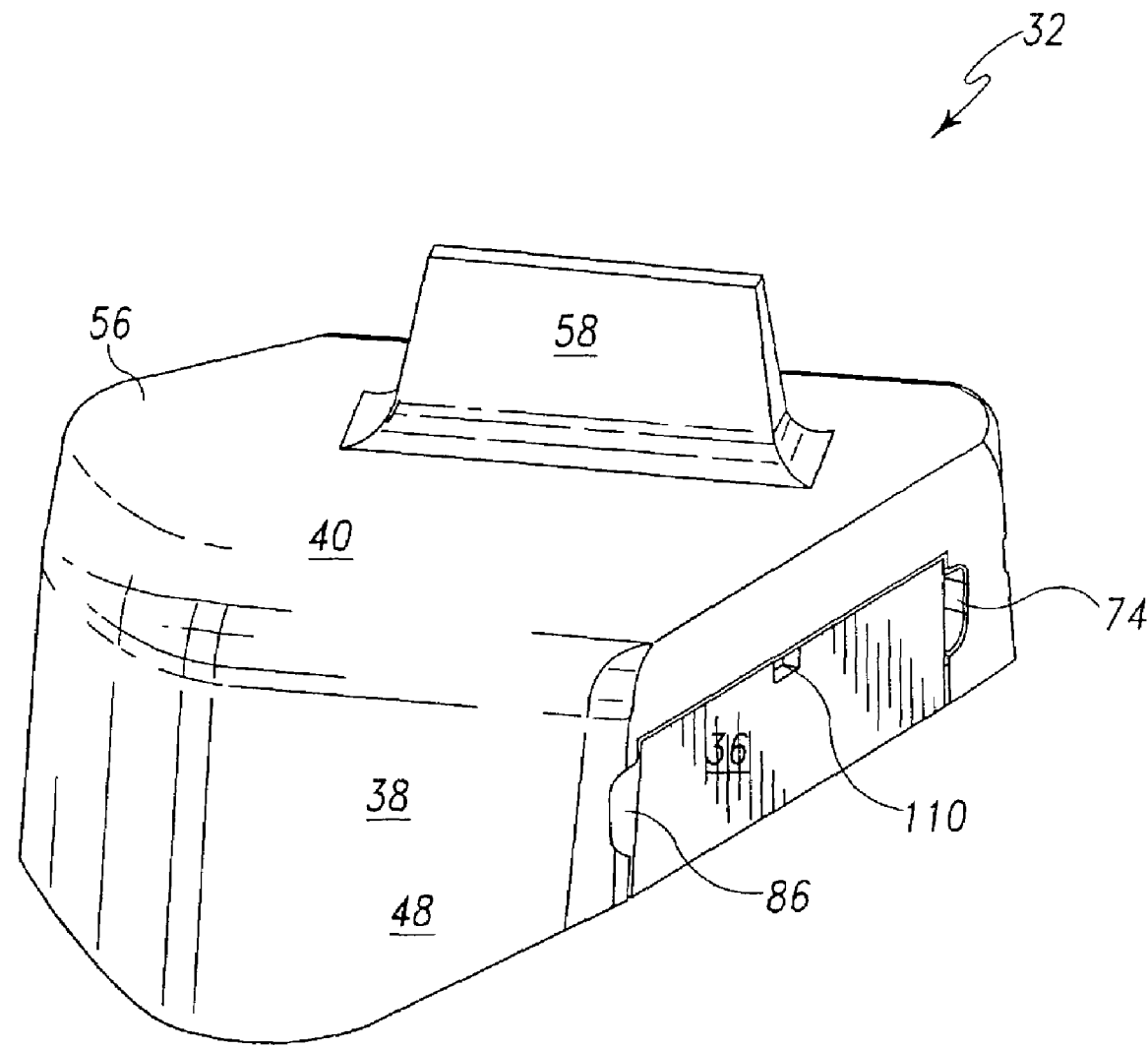
FIG. 7 is a perspective view of the tibial assembly of FIG. 1.

As the ribs 118, 124 are fully received in the slots 74, 86 (i.e., the ribs 118, 124 begin to engage the posterior ends 82, 94 of the slots 74, 86), the latch 106 passes by the retaining wall 66. The bias of the inferior edges 78, 90 of the slots 74, 86 against the ribs 118, 124 pushes the bearing component 36 in the inferior-to-superior direction 60 such that the latch 106 latches behind and onto the retaining wall 66. Thus, the latch 106 enters into a snap-locking engagement or matingly couples with the retaining wall 66, and the bearing component 36 is snap-locked to the tibial component 38. FIG. 7 illustrates the assembled tibial assembly 32 with the bearing component 36 in snap-locking engagement with the tibial component 38.

Figure 8:
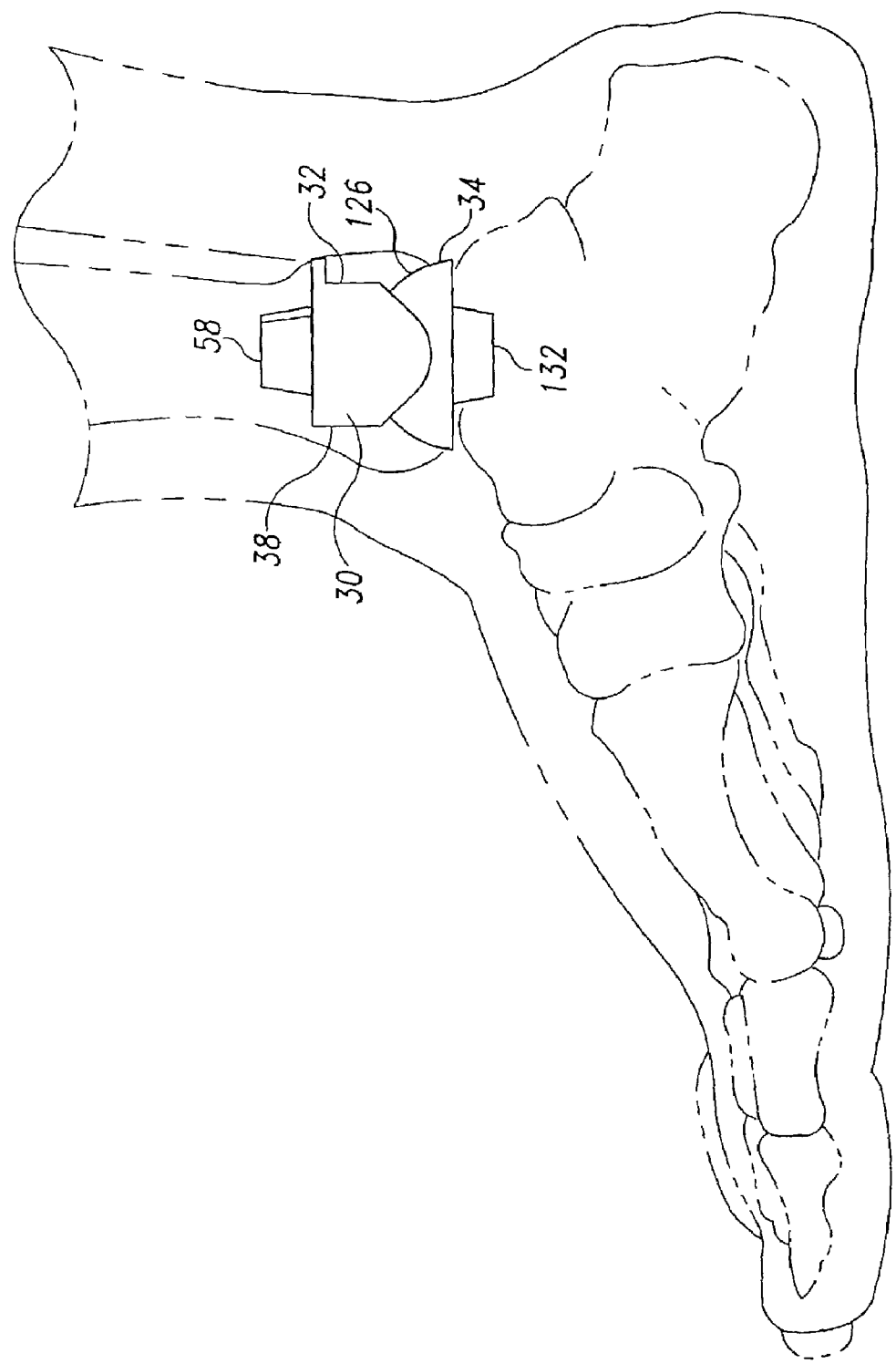
FIG. 8 is a side view of the ankle prosthesis of FIG. 1 implanted in a patient's ankle.

As shown in FIGS. 6 and 8, the ankle prosthesis 30 is implanted with the talar component 34 attaching to the talus and the tibial component 38 attaching to the tibia and fibula bones with the superior wall 40 bridging the bones. The tibial fin 58 extends up into the tibia bone when implanted and positions the tibial component 38 correctly. In a similar manner, the talar fin 132 extends down into the talus to keep the talar component 34 properly aligned when implanted.

An externally threaded implanting tool (not shown) can be screwed into the screw hole 70 and can thereafter be used to guide the tibial assembly 32 into the patient's ankle. After the tibial assembly 32 has been implanted in the patient's ankle, the implanting tool can be unscrewed from the screw hole 70 in order to disengage the implanting tool from the tibial assembly 32. The ankle prosthesis 30 can be implanted with or without the use of bone cement.

In the event that the bearing component 36 becomes worn out or damaged, the bearing component 36 can be easily removed from the tibial component 38 and replaced with a new bearing component 36 without removing the tibial component 38 from the patient's ankle. Specifically, the surgeon can insert the end of the removal tool 112 into the notch 110 and press the tool 112 in the superior-to-inferior direction 50. The force of the tool 112 deforms the resilient bearing component 36 such that the latch 106 is moved out of its snap-fit engagement with the retaining wall 66. Thus, the bearing component 36 is released and unlocked from the tibial component 38.

The surgeon can then pull the bearing component 36 in a posterior-to-anterior direction 136 until the bearing component 36 is fully disengaged from the tibial component 38. A new bearing component 36 is then brought into engagement with and locked to the tibial component 38 by moving the new bearing component 36 in the anterior-to-posterior direction 54. The details of the method of locking the new bearing component 36 to the tibial component 38 are similar to the method described above for locking the original bearing component 36 to the tibial component 38, and thus are not discussed in detail herein.

Figure 9:
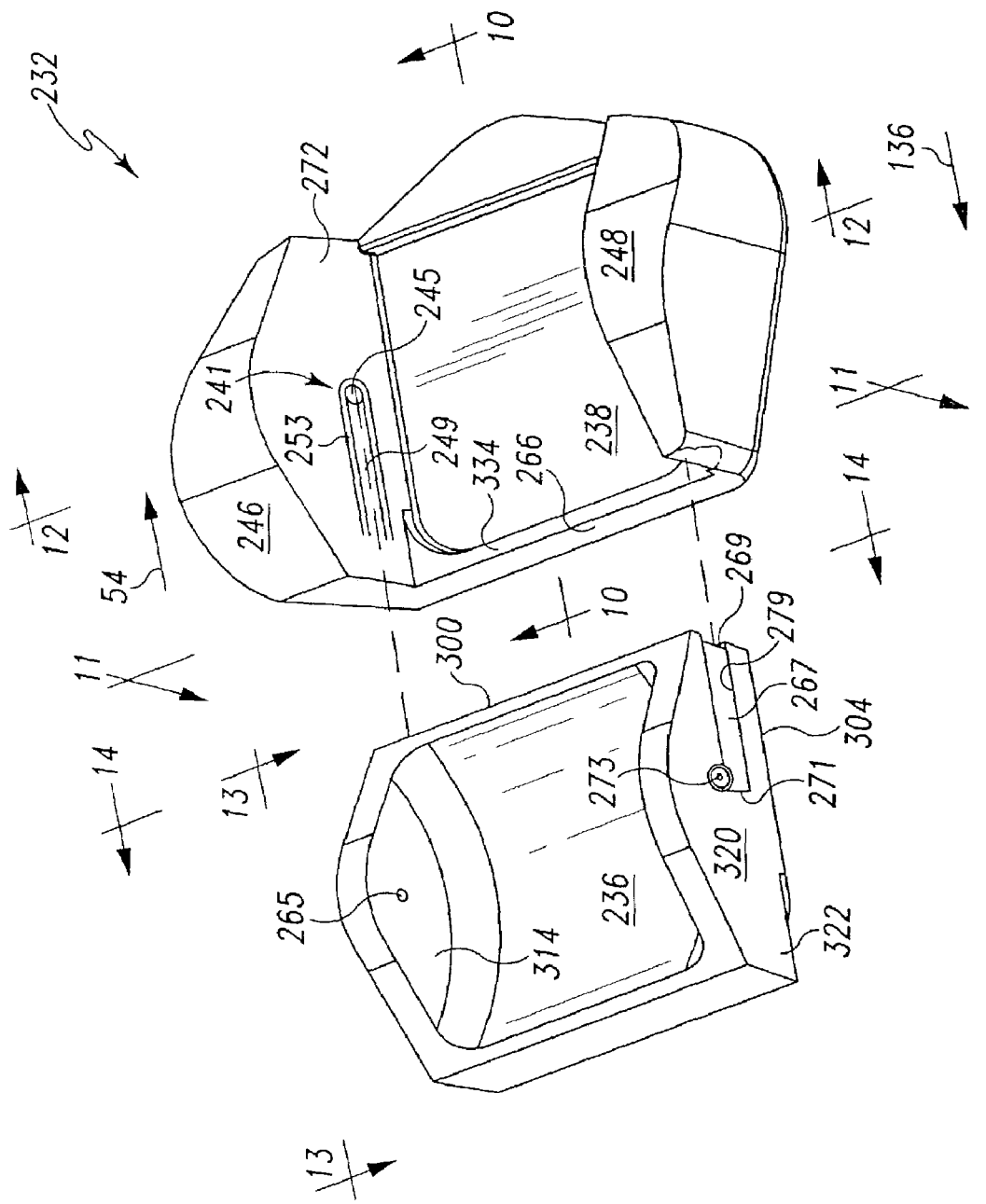
FIG. 9 is a perspective, exploded view of another embodiment of a tibial assembly of the present invention.
Figure 10:
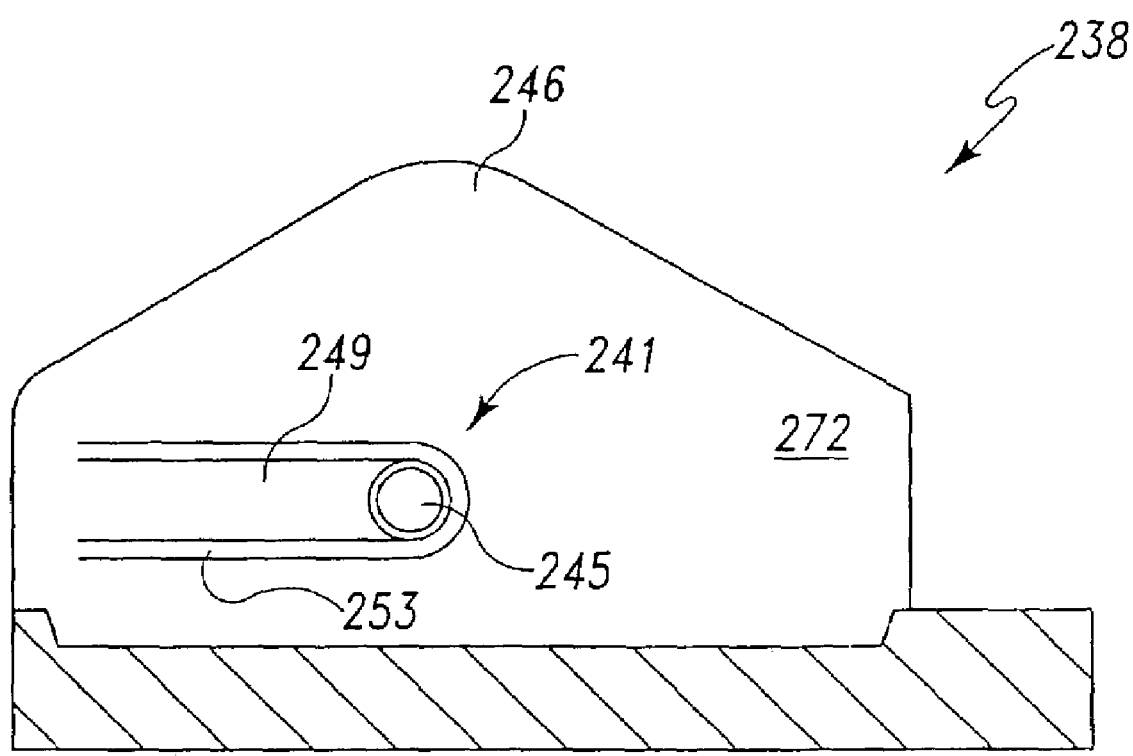
FIG. 10 is a side sectional view of the tibial component along line 10—10 in FIG. 9.
Figure 11:
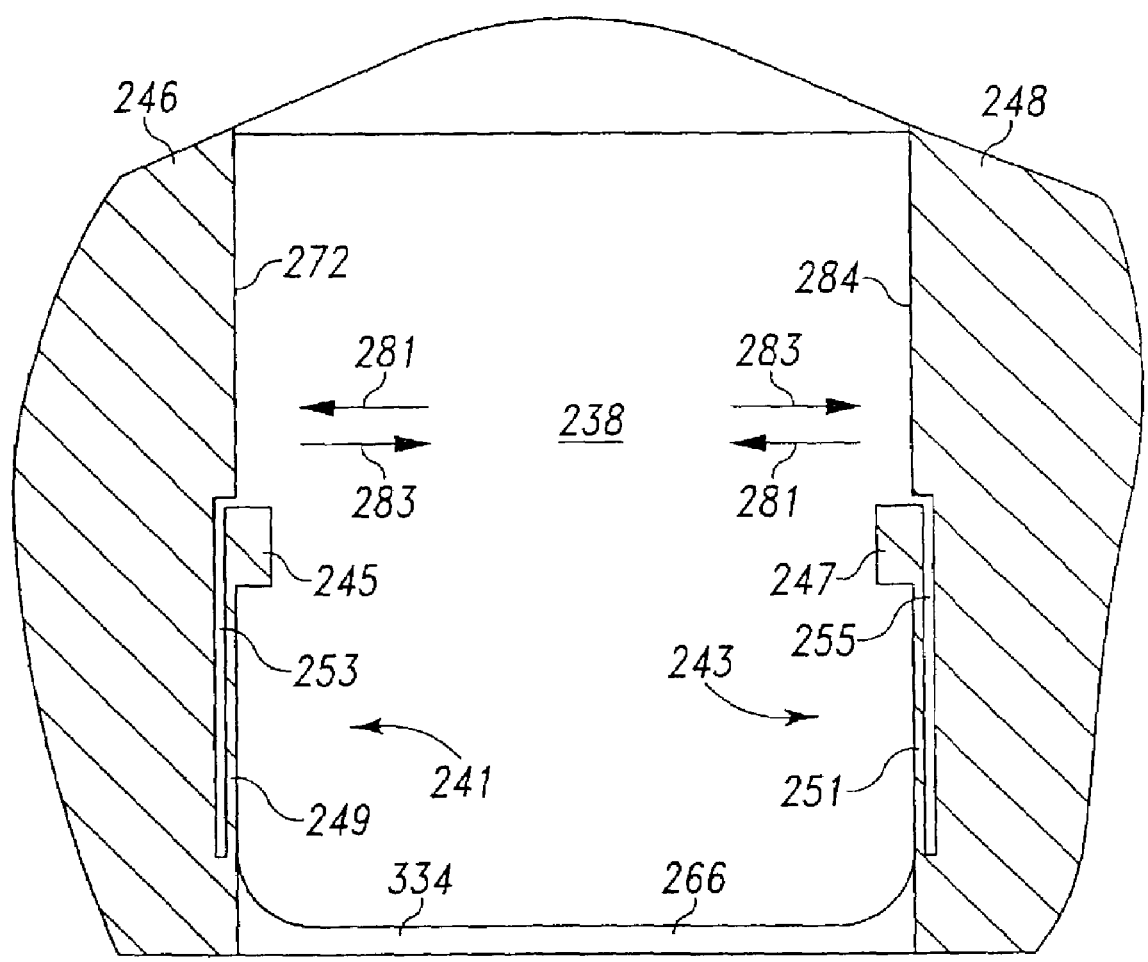
FIG. 11 is an enlarged top sectional view of the tibial component along line 11—11 in FIG. 9.
Figure 12:
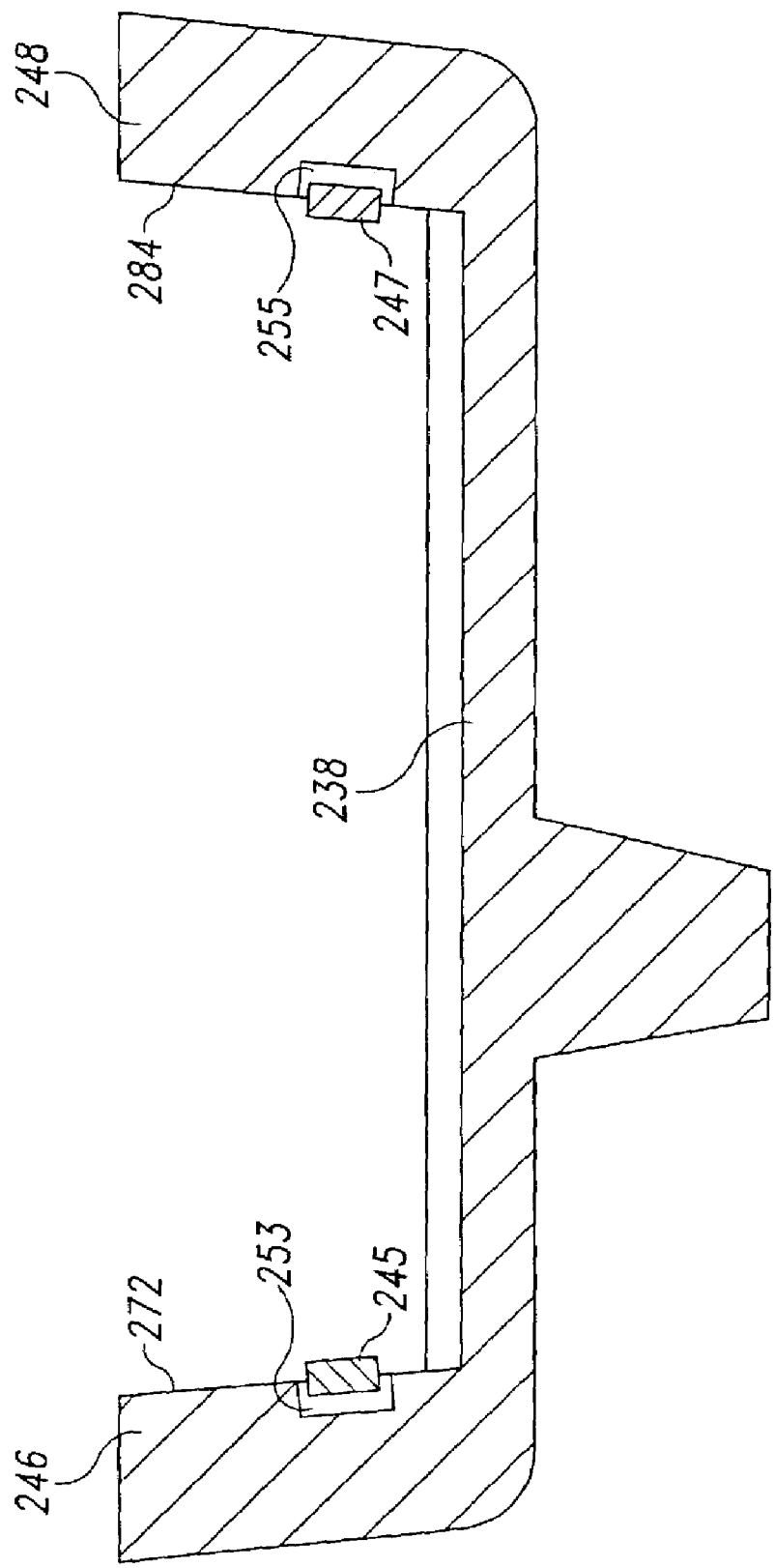
FIG. 12 is an enlarged front sectional view of the tibial component along line 12—12 in FIG. 9.

In another embodiment (FIG. 9), an ankle prosthesis for a right ankle includes a tibial assembly 232 having a resilient bearing component 236 and a tibial component 238. The tibial component 238 includes a medial bearing-retaining device 241 (FIG. 10) and a lateral bearing-retaining device 243 (FIG. 11) which are mirror images of each other. The bearing-retaining devices 241, 243 have respective medial and lateral projections or buttons 245, 247 (FIG. 12) attached to the distal ends of respective medial and lateral leaf springs 249, 251. The leaf springs 249, 251 have anterior-posterior orientations. The bearing-retaining devices 241, 243 are disposed in respective medial and lateral grooves 253, 255 on respective inner surfaces 272, 284 of a medial wall 246 and a lateral wall 248. The grooves 253, 255 also have anterior-posterior orientations.

Figure 13:
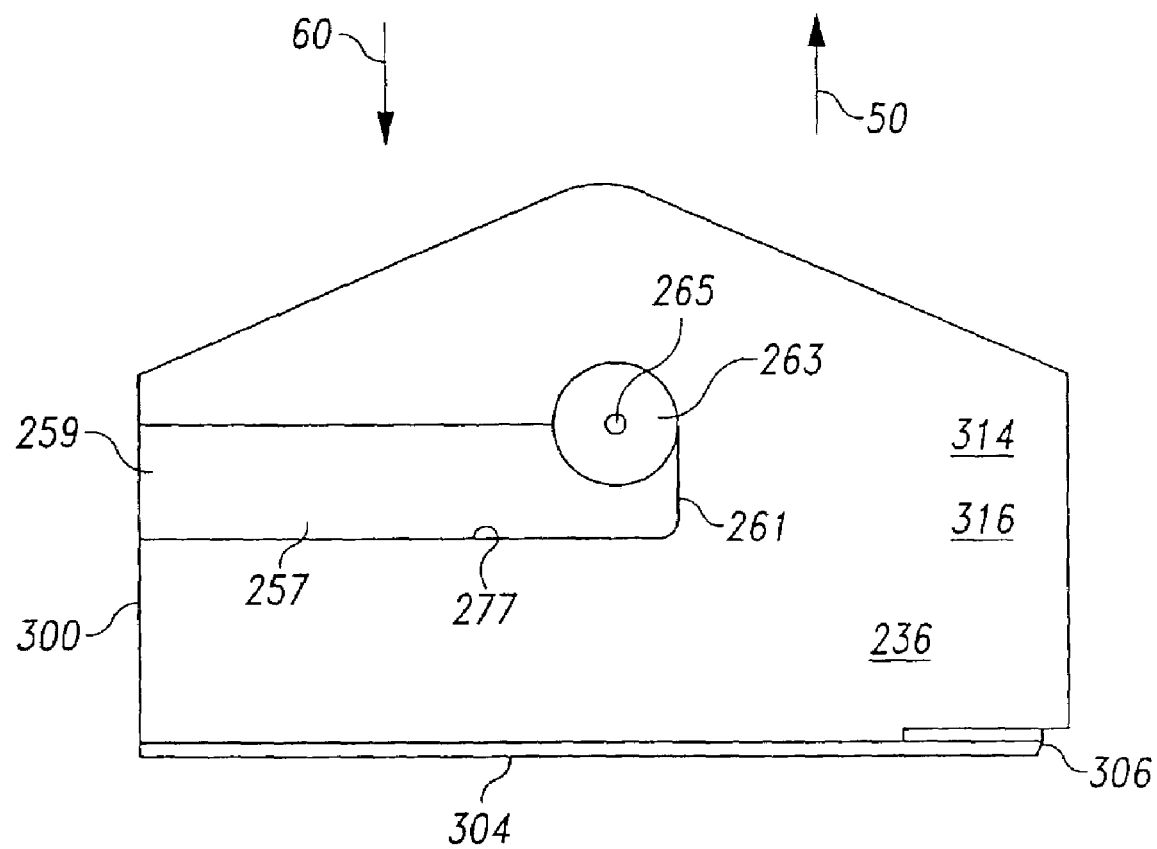
FIG. 13 is a side view of the bearing component along line 13—13 in FIG. 9.
Figure 14:
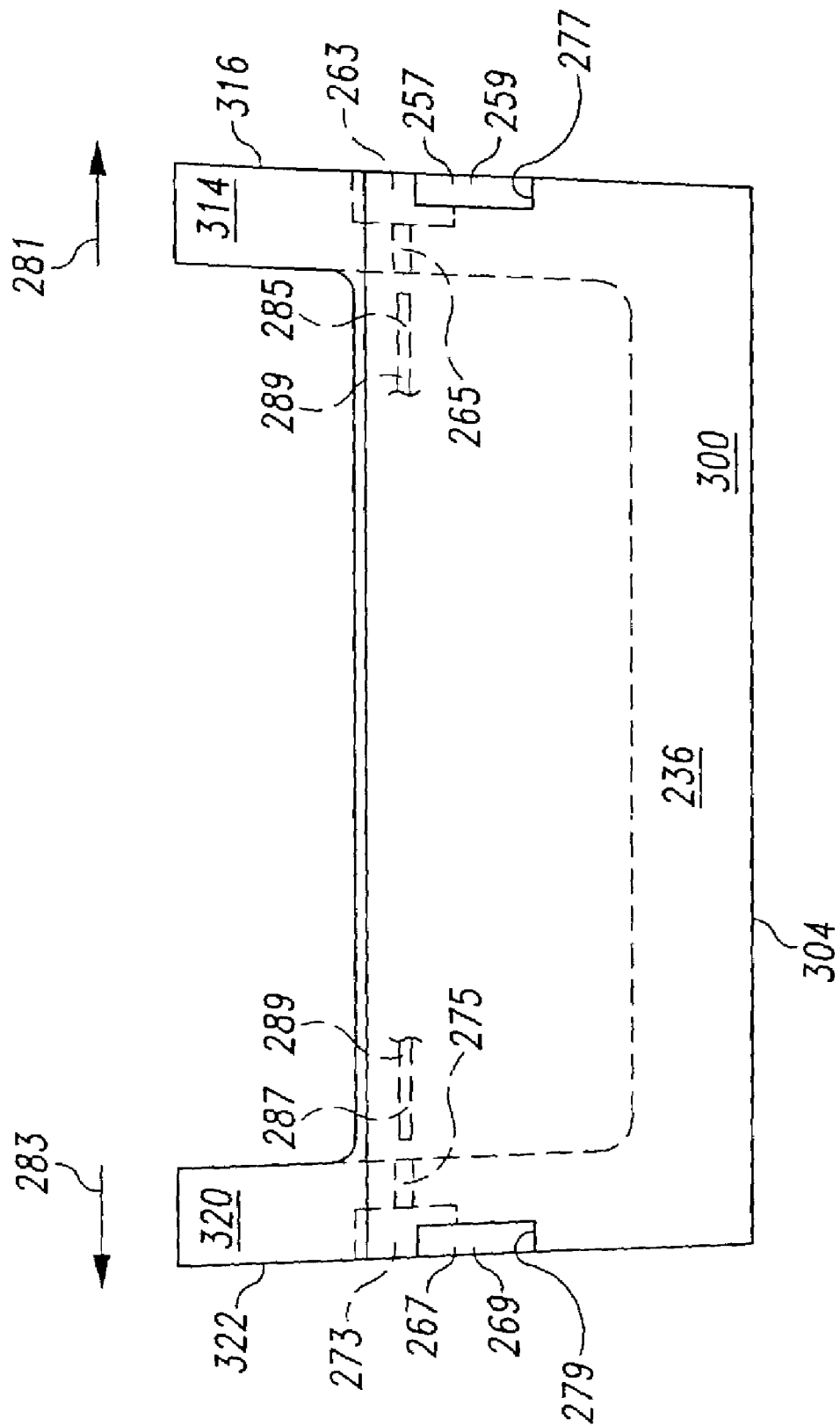
FIG. 14 is a rear view of the bearing component along line 14—14 in FIG. 9.

An outer surface 316 (FIG. 13) of a medial side portion 314 of the bearing component 236 includes a medial slot 257 having an anterior-posterior orientation and an opening 259 in a posterior side 300 of the bearing component 236. At an anterior end 261 of the slot 257 is a cylindrical recess 263 in communication with a throughhole 265, best seen in FIG. 14, extending through the medial side portion 314. The recess 263 is offset from the slot 257 in the superior-to-inferior direction 50.

An outer surface 322 of a lateral side portion 320 includes a lateral slot 267 having an anterior-posterior orientation and an opening 269 in the posterior side 300. At an anterior end 271 of the slot 267 is a cylindrical recess 273 in communication with a throughhole 275 extending through the lateral side portion 320. The recess 273 is offset from the slot 267 in the superior-to-inferior direction 50. In the embodiment shown, the slots 257, 267, recesses 263, 273, and throughholes 265, 275 are mirror images of each other. Other aspects of the tibial component 238 and the bearing component 236 are substantially similar to the tibial component 38 and the bearing component 36, respectively, and thus are not discussed in detail herein.

During assembly, the bearing component 236 is moved in the anterior-to-posterior direction 54 to thereby engage the tibial component 238. When the bearing component 236 is approximately half-way inserted into the tibial component 238, the medial button 245 and the lateral button 247 enter into the medial slot opening 259 and the lateral slot opening 269, respectively. The buttons 245, 247 are biased in directions 281 and 283, respectively, by the slots 257, 267, respectively. As the bearing component 236 progresses in the anterior-to-posterior direction 54, a superior surface 304 of the bearing component 236 is biased against an inferior surface 334 of a retaining wall 266.

As the buttons 245, 247 are fully received in the slots 257, 267 (i.e., the buttons 245, 247 begin to engage the anterior ends 261, 271 of the slots 257, 267), a latch 306 passes by the retaining wall 266. The bias of the buttons 245, 247 against superior edges 277, 279 of the slots 257, 267, respectively, pushes the bearing component 236 in the inferior-to-superior direction 60 such that the latch 306 latches onto the retaining wall 266. Thus, the latch 306 enters into a snap-locking engagement with the retaining wall 266, and the bearing component 236 is snap-locked to the tibial component 238.

As the buttons 245, 247 begin to engage the anterior ends 261, 271 of the slots 257, 267, and the bearing component 236 is pushed in the inferior-to-superior direction 60, the bias of the leaf springs 249, 251 pushes the buttons 245, 247 in directions 283, 281, respectively, into the cylindrical recesses 263, 273. Thus, the bearing component 236 is locked to the tibial component 238 by virtue of the buttons 245, 247 being seated in the respective recesses 263, 273, and by virtue of the latch 306 being in snap-locking engagement with the retaining wall 266. The details of implanting the tibial assembly 232 into a patient's ankle are substantially similar to those of implanting the tibial assembly 32, and thus are not discussed in detail herein.

In the event that the bearing component 236 becomes worn out or damaged, the bearing component 236 can be easily removed from the tibial component 238 and replaced with a new bearing component 236 without removing the tibial component 238 from the patient's ankle. Specifically, the surgeon can insert the opposing pins 285, 287 of a partially shown removal tool 289 into the throughholes 265, 275 and push the buttons 245, 247 in directions 281, 283 out of the recesses 263, 273. With the bearing component 236 thus unlocked from the tibial component 238, the removal tool 289 can then be used to push the bearing component 236 in the superior-to-inferior direction 50. The movement of the bearing component 236 in the superior-to-inferior direction 50 results in the buttons 245, 247 being received in the slots 257, 267 and the latch 306 being moved out of its snap-fit engagement with the retaining wall 266. Thus, the bearing component 236 is released and unlocked from the tibial component 238.

The surgeon can then pull the bearing component 236, possibly with the removal tool 289, in the posterior-to-anterior direction 136 until the bearing component 236 is fully disengaged from the tibial component 238. A new bearing component 236 is then brought into engagement with and locked to the tibial component 238 by moving the new bearing component 236 in the anterior-to-posterior direction 54. The details of the method of locking the new bearing component 236 to the tibial component 238 are similar to the method described above for locking the original bearing component 236 to the tibial component 238, and thus are not discussed in detail herein.

Figure 15:
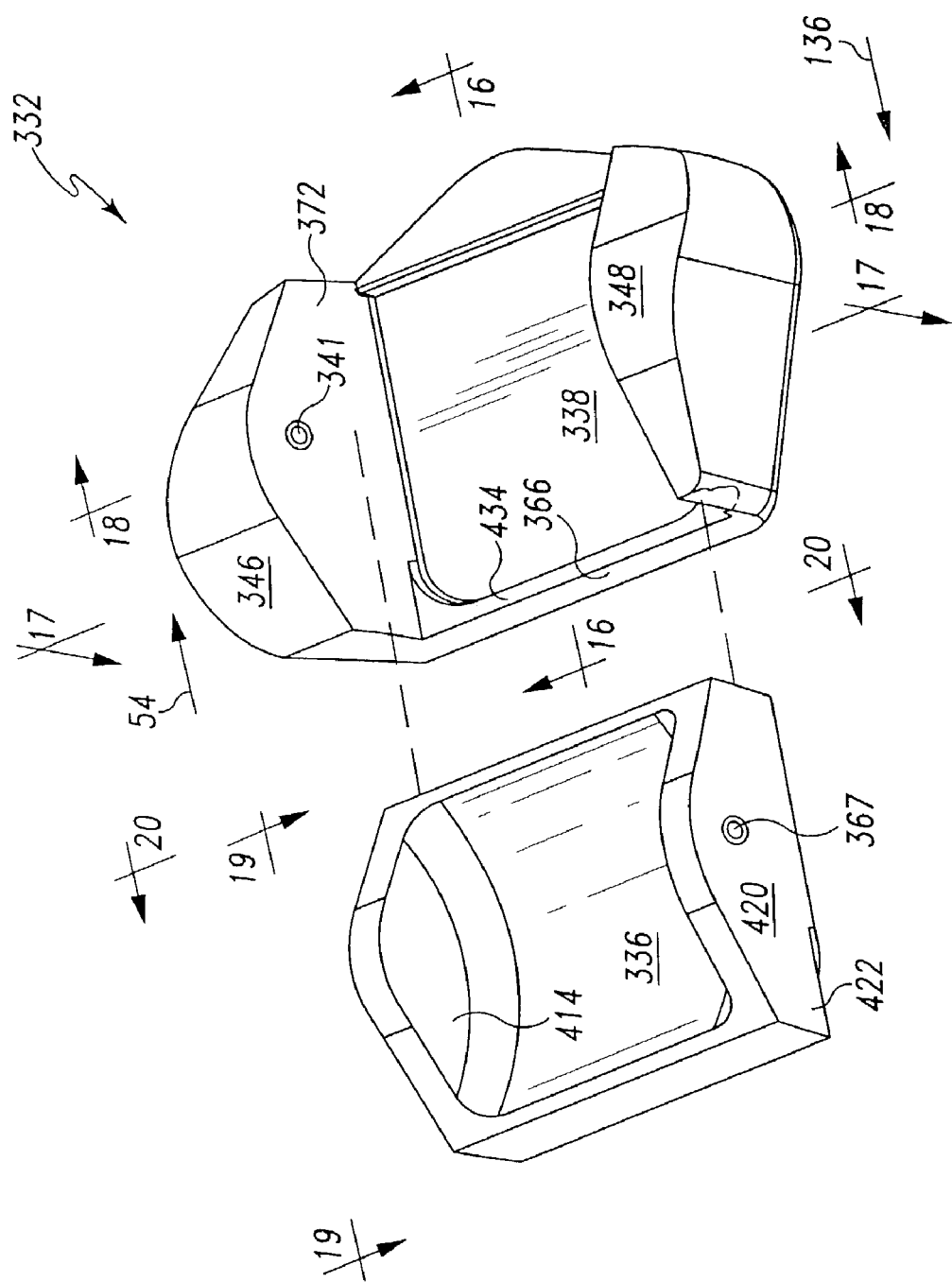
FIG. 15 is a perspective, exploded view of yet another embodiment of a tibial assembly of the present invention.
Figure 16:
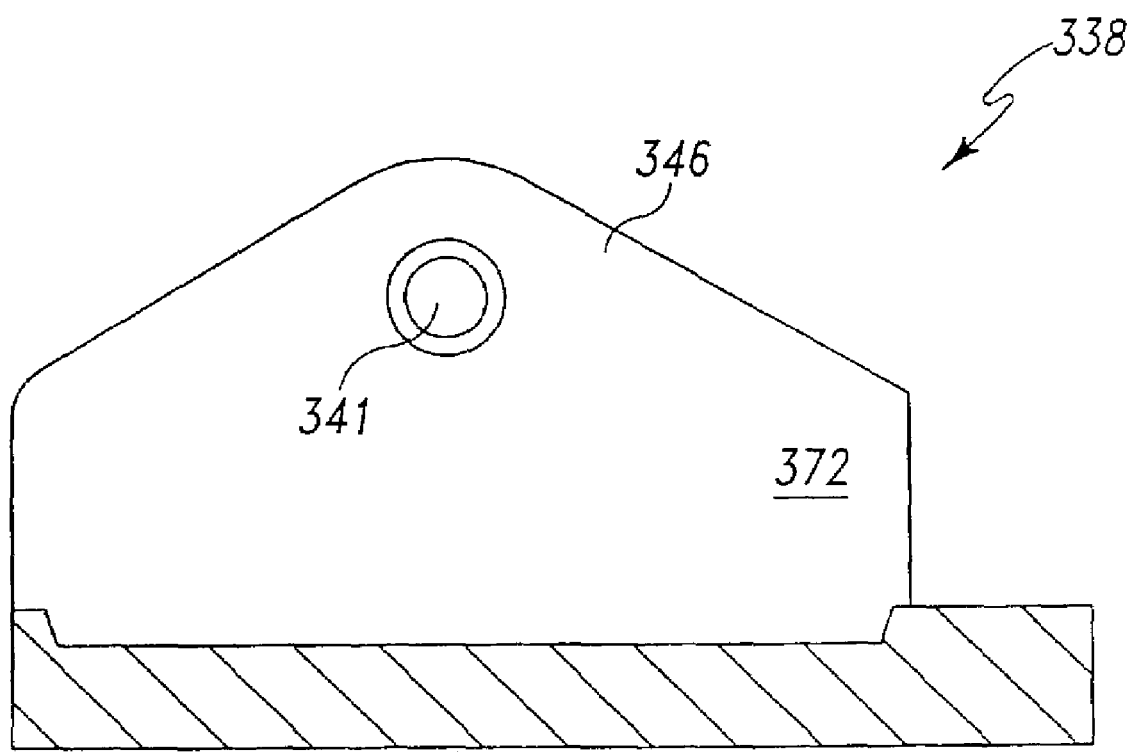
FIG. 16 is a side sectional view of the tibial component along line 16—16 in FIG. 15.
Figure 17:
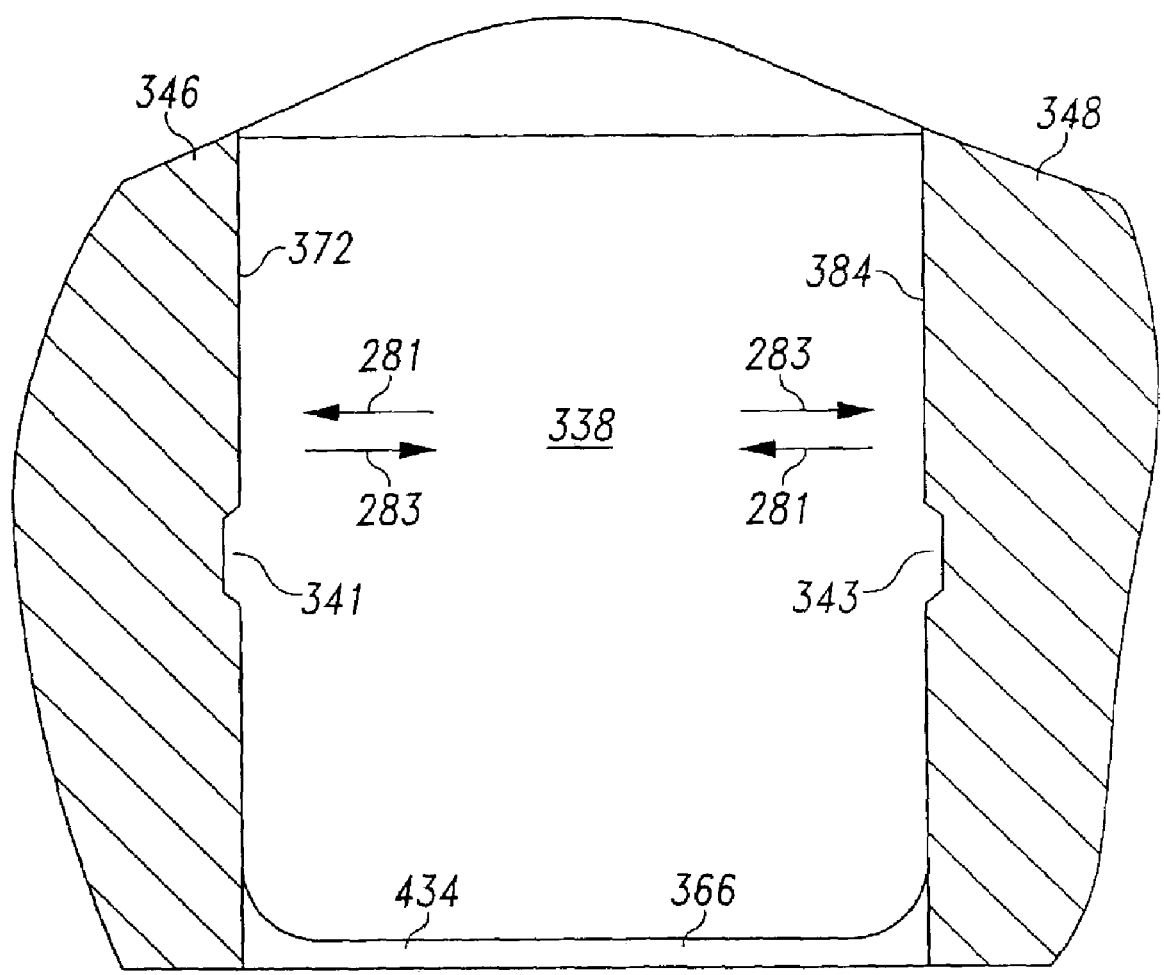
FIG. 17 is an enlarged top sectional view of the tibial component along line 17—17 in FIG. 15.
Figure 18:
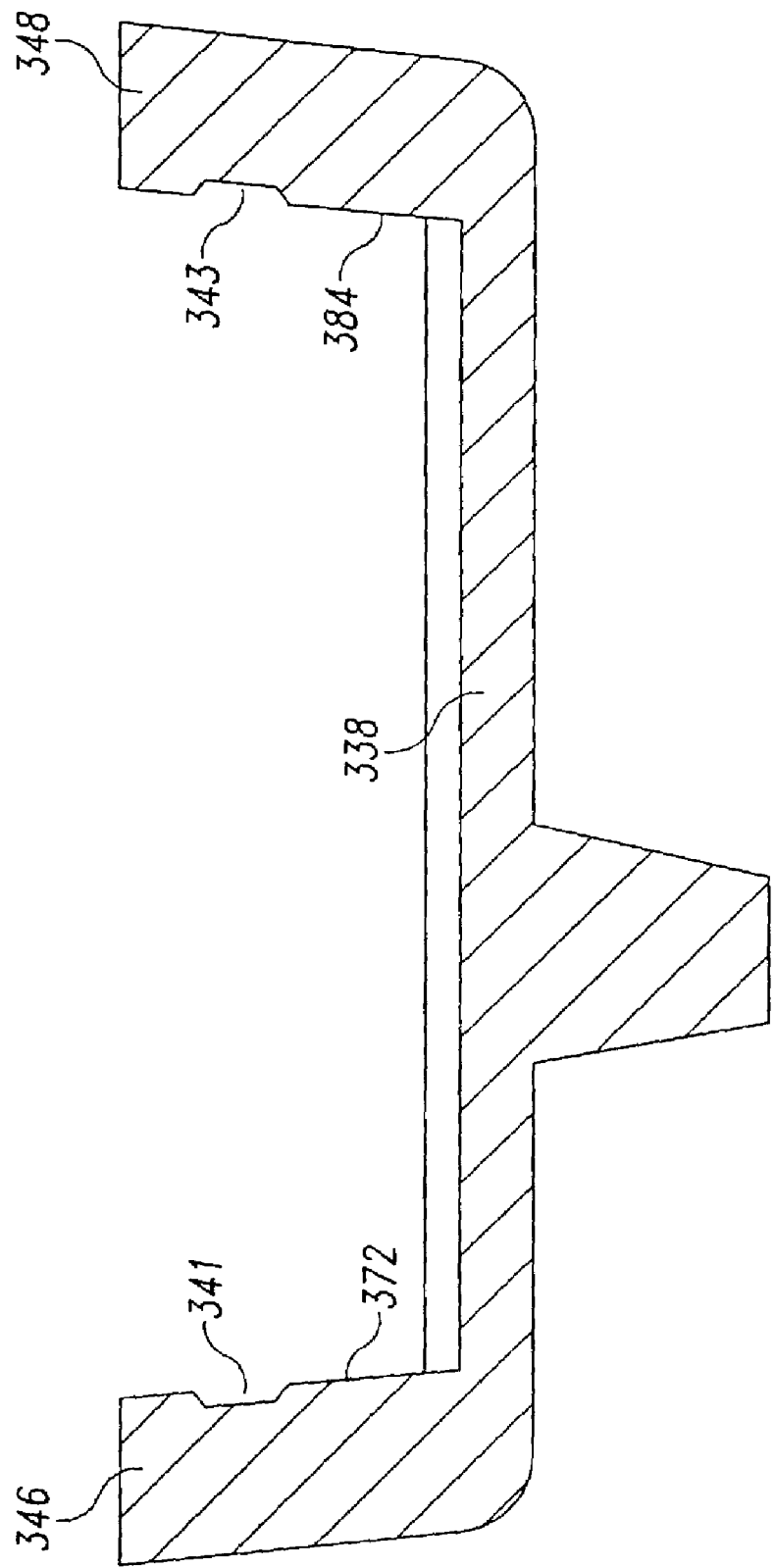
FIG. 18 is an enlarged front sectional view of the tibial component along line 18—18 in FIG. 15.

In yet another embodiment (FIG. 15), an ankle prosthesis for a right ankle includes a tibial assembly 332 having a resilient bearing component 336 and a tibial component 338. The tibial component 338 includes a medial bearing-retaining recess 341 (FIG. 16) and a lateral bearing-retaining recess 343 (FIGS. 17 and 18) which are mirror images of each other. The recesses 341 and 343 are frustoconically-shaped and are disposed in respective inner surfaces 372, 384 of a medial wall 346 and a lateral wall 348.

Figure 19:
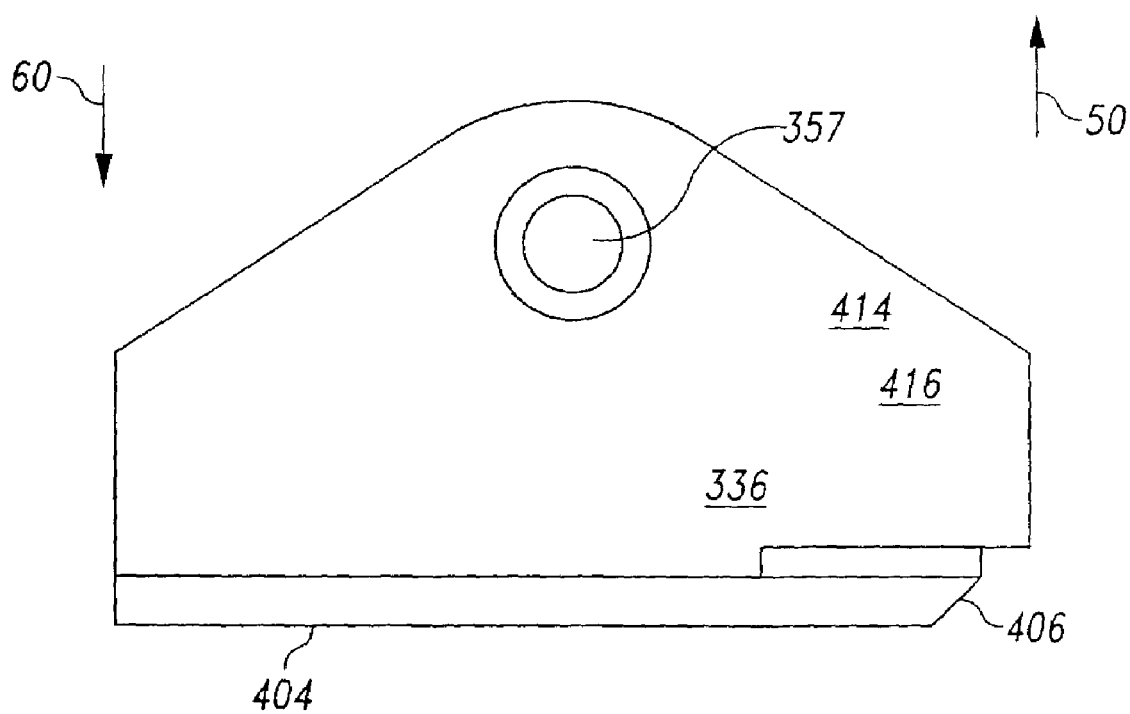
FIG. 19 is a side view of the bearing component along line 19—19 in FIG. 15.
Figure 20:
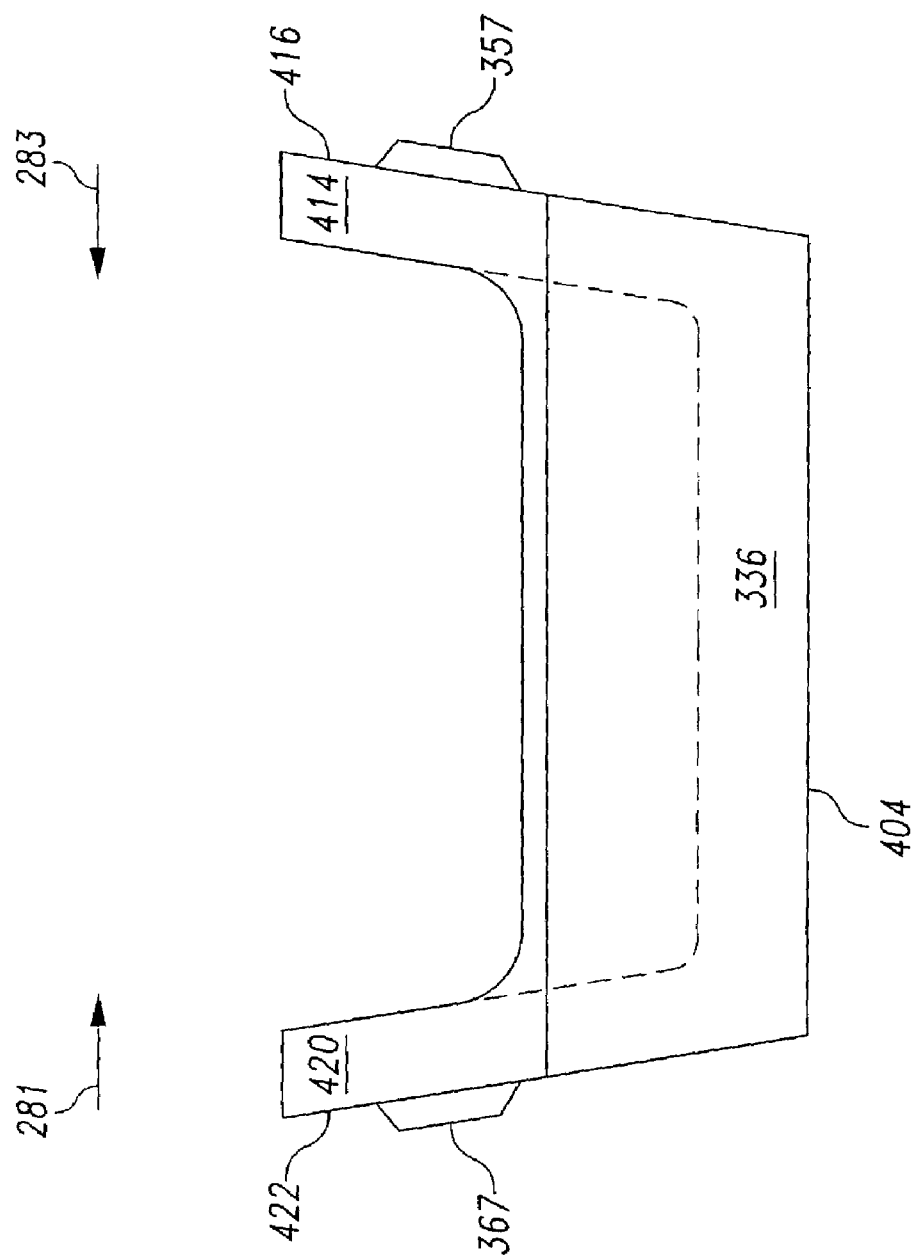
FIG. 20 is a rear view of the bearing component along line 20—20 in FIG. 15.

An outer surface 416 (FIG. 19) of a medial side portion 414 of the bearing component 336 includes a frustoconically-shaped medial projection 357. An outer surface 422 of a lateral side portion 420 includes a frustoconically-shaped lateral projection 367. In the embodiment shown, the projections 357, 367 are mirror images of each other. Other aspects of the tibial component 338 and the bearing component 336 are substantially similar to the tibial component 38 and the bearing component 36, respectively, and thus are not discussed in detail herein.

During assembly, the bearing component 336 is moved in the anterior-to-posterior direction 54 to thereby engage the tibial component 338. As the bearing component 336 moves in the anterior-to-posterior direction 54, the projection 357 and the medial side portion 414 are biased in direction 283 by the inner surface 372. Similarly, the projection 367 and the lateral side portion 420 are biased in direction 281 by the inner surface 384. As the bearing component 336 progresses in the anterior-to-posterior direction 54, a superior surface 404 of the bearing component 336 is biased against an inferior surface 434 of a retaining wall 366. When the bearing component 336 is approximately half-way inserted into the tibial component 338, the medial projection 357 and the lateral projection 367 become aligned with the recesses 341, 343, respectively. The resiliency of the medial side portion 414 and the lateral side portion 420 causes the projections 357, 367 to move in directions 281, 283, respectively, and become seated in the recesses 341, 343.

As the projections 357, 367 are fully received in the recesses 341, 343, a latch 406 passes by the retaining wall 366. The bias of the recesses 341, 343 against the projections 357, 367, respectively, pushes the bearing component 336 in the inferior-to-superior direction 60 such that the latch 406 latches onto the retaining wall 366. Thus, the latch 306 enters into a snap-locking engagement with the retaining wall 366, and the bearing component 336 is snap-locked to the tibial component 338. The bearing component 336 is locked to the tibial component 338 by virtue of the projections 357, 367 being seated in the respective recesses 341, 343, and by virtue of the latch 406 being in snap-locking engagement with the retaining wall 366. The details of implanting the tibial assembly 332 into a patient's ankle are substantially similar to those of implanting the tibial assembly 32, and thus are not discussed in detail herein.

In the event that the bearing component 336 becomes worn out or damaged, the bearing component 336 can be easily removed from the tibial component 338 and replaced with a new bearing component 336 without removing the tibial component 238 from the patient's ankle. Specifically, the surgeon can pull the bearing component 336 in the superior-to-inferior direction 50, possibly with the use of a removal tool. The movement of the bearing component 336 in the superior-to-inferior direction 50 results in the projections 357, 367 being removed from the recesses 341, 343 and the latch 406 being moved out of its snap-fit engagement with the retaining wall 366. Thus, the bearing component 336 is released and unlocked from the tibial component 338.

The surgeon can then pull the bearing component 336, possibly with a removal tool, in the posterior-to-anterior direction 136 until the bearing component 336 is fully disengaged from the tibial component 338. A new bearing component 336 is then brought into engagement with and locked to the tibial component 338 by moving the new bearing component 336 in the anterior-to-posterior direction 54. The details of the method of locking the new bearing component 336 to the tibial component 338 are similar to the method described above for locking the original bearing component 336 to the tibial component 338, and thus are not discussed in detail herein.

In the embodiments discussed above, the bearing component and the tibial component are shown as having mating male and female retaining mechanisms. It is to be understood that it is arbitrary which of the bearing component and the tibial component includes the male retaining mechanism or the female retaining mechanism. That is, the male retaining mechanism can be included on either the bearing component or the tibial component. For example, the bearing component 336 has been shown as including projections 357, 367, and the tibial component 338 has been shown as including recesses 341, 343. However, it is also possible for the bearing component to include the recesses, and the tibial component to include the projections.

The tibial component and the talar component of the ankle prosthesis can be formed of conventional bio-compatible metals or suitably strong materials. For instance, the tibial component can be formed of a titanium alloy and the talar component can be formed of a cobalt-chromium alloy or stainless steel alloy.

The tibial component and the talar component can be porous coated depending upon the preferred application. The tibial assembly and the talar component can be provided in various sizes and shapes to accommodate various patient ankle sizes and shapes.

In one preferred embodiment, the ankle prosthesis is provided to the orthopaedic surgeon in a kit of various sizes, dimensions and/or shapes of tibial assemblies and talar components. The kit can include all of the components necessary to perform any of the replacement surgeries described above. The components can be assembled in the operating room, if necessary.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A method comprising:
providing an ankle prosthesis having (i) a tibial component defining a bearing space and an access opening, and (ii) a first bearing component;
attaching the tibial component to a distal end portion of a tibia of a patient so that the access opening faces anteriorly;
placing the first bearing component into the bearing space defined by the tibial component;
after a period of use of the ankle prosthesis in the patient and while the tibial component is attached to tibia, removing the first bearing component from the tibial component by advancing the first bearing component in a posterior-to-anterior direction, wherein the first bearing component is advanced out of the bearing space and through the access opening in response to the first bearing component being advanced in the posterior-to-anterior direction;
providing a second bearing component; and
after the first bearing component removing step and while the tibial component is attached to tibia, advancing the second bearing component in an anterior-to-posterior direction, wherein the second bearing component is advanced through the access opening and into the bearing space in response to the second bearing component being advanced in the anterior-to-posterior direction.

2. The method of claim 1, wherein the second bearing component and the tibial component become snap-locked together in response to the second bearing component being advanced in the anterior-to-posterior direction.

3. The method of claim 2, wherein:
the second bearing component includes a latch member, the tibial component includes a retaining wall portion, and after the second bearing component and the tibial component become snap-locked together, advancement of the second bearing component in the posterior-to-anterior direction is inhibited due to contact between the retaining wall and the latch member.

4. The method of claim 1, wherein:
the second bearing component has an articular surface, and
the articular surface faces inferiorly during advancement of the second bearing component through the access opening and into the bearing space.

5. The method of claim 1, wherein:
the tibial component includes (i) a superior wall, (ii) a medial wall extending inferiorly from the superior wall, and (iii) a lateral wall spaced apart from the medial wall and extending inferiorly from the superior wall,
the medial wall defines a first anteriorly-to-posteriorly extending slot that faces the bearing space, and
the lateral wall defines a second anteriorly-to-posteriorly extending slot that faces the bearing space.

6. The method of claim 5, wherein the second bearing component includes:
a lateral side portion,
a medial side portion,
a first anteriorly-to-posteriorly extending rib on the medial side portion; and
a second anteriorly-to-posteriorly extending rib on the lateral side portion.

7. The method of claim 6, wherein the first rib is received in the first slot and the second rib is received in the second slot during advancement of the second bearing component in the anterior-to-posterior direction.

8. A method comprising:
providing an ankle prosthesis having (i) a tibial component defining a bearing space and an access opening, (ii) a first bearing component having a first articular surface, and (iii) a talar component having a second articular surface;
attaching the tibial component to a distal end portion of a tibia of a patient so that the access opening faces anteriorly;
placing the first bearing component into the bearing space defined by the tibial component;
attaching the talar component to a talus of the patient so that the second articular surface faces superiorly;
placing the first articular surface of the first bearing component into contact with the second articular surface of the talar component;
after a period of use of the ankle prosthesis in the patient and while the tibial component is attached to tibia, removing the first bearing component from the tibial component by advancing the first bearing component in a posterior-to-anterior direction, wherein the first bearing component is advanced out of the bearing space and through the access opening in response to the first bearing component being advanced in the posterior-to-anterior direction;

providing a second bearing component having a third articular surface;

after the first bearing component removing step and while the tibial component is attached to tibia, advancing the second bearing component in an anterior-to-posterior direction, wherein the second bearing component is advanced through the access opening and into the bearing space in response to the second bearing component being advanced in the anterior-to-posterior direction; and after the second bearing component advancing step, placing the third articular surface of the second bearing component into contact with the second articular surface of the talar component.

9. The method of claim 8, wherein the second bearing component and the tibial component become snap-locked together in response to the second bearing component being advanced in the anterior-to-posterior direction.

10. The method of claim 9, wherein:
the second bearing component includes a latch member,
the tibial component includes a retaining wall portion, and
after the second bearing component and the tibial component become snap-locked together, advancement of the second bearing component in the posterior-to-anterior direction is inhibited due to contact between the retaining wall and the latch member.

11. The method of claim 8, wherein the third articular surface faces inferiorly during advancement of the second bearing component through the access opening and into the bearing space.

12. The method of claim 8, wherein:
the tibial component includes (i) a superior wall, (ii) a medial wall extending inferiorly from the superior wall, and (iii) a lateral wall spaced apart from the medial wall and extending inferiorly from the superior wall,
the medial wall defines a first anteriorly-to-posteriorly extending slot that faces the bearing space, and
the lateral wall defines a second anteriorly-to-posteriorly extending slot that faces the bearing space.

13. The method of claim 12, wherein the second bearing component includes:
a lateral side portion,
a medial side portion,
a first anteriorly-to-posteriorly extending rib on the medial side portion, and
a second anteriorly-to-posteriorly extending rib on the lateral side portion.

14. The method of claim 13, wherein the first rib is received in the first slot and the second rib is received in the second slot during advancement of the second bearing component in the anterior-to-posterior direction.

15. A method comprising:
providing an ankle prosthesis having (i) a tibial component defining a bearing space and an access opening, and (ii) a first bearing component;

attaching the tibial component to a distal end portion of a tibia of a patient so that the access opening faces anteriorly;

placing the first bearing component into the bearing space defined by the tibial component;

after a period of use of the ankle prosthesis in the patient and while the tibial component is attached to tibia, removing the first bearing component from the tibial component by advancing the first bearing component in a posterior-to-anterior direction, wherein the first bearing component is advanced out of the bearing space and through the access opening in response to the first bearing component being advanced in the posterior-to-anterior direction;

after the first bearing component removing step and while the tibial component is attached to tibia, advancing a second bearing component in an anterior-to-posterior direction through the access opening and into the bearing space, wherein the second bearing component and the tibial component become snap-locked together in response to the second bearing component being advanced in the anterior-to-posterior direction.

16. The method of claim 15, wherein:
the second bearing component includes a latch member,
the tibial component includes a retaining member, and
after the second bearing component and the tibial component become snap-locked together, advancement of the second bearing component in the posterior-to-anterior direction is inhibited due to contact between the retaining member and the latch member.

17. The method of claim 15, wherein the third articular surface faces inferiorly during advancement of the second bearing component through the access opening and into the bearing space.

18. The method of claim 15, wherein:
the tibial component includes (i) a superior wall, (ii) a medial wall extending inferiorly from the superior wall, and (iii) a lateral wall spaced apart from the medial wall and extending inferiorly from the superior wall,
the medial wall defines a first anteriorly-to-posteriorly extending slot that faces the bearing space, and
the lateral wall defines a second anteriorly-to-posteriorly extending slot that faces the bearing space.

19. The method of claim 18, wherein the second bearing component includes:
a lateral side portion,
a medial side portion,
a first anteriorly-to-posteriorly extending rib on the medial side portion, and
a second anteriorly-to-posteriorly extending rib on the lateral side portion.

20. The method of claim 19, wherein the first rib is received in the first slot and the second rib is received in the second slot during advancement of the second bearing component in the anterior-to-posterior direction.

* * * * *